United States Patent
Igumenova et al.

(10) Patent No.: US 12,187,765 B2
(45) Date of Patent: Jan. 7, 2025

(54) PREPARATION OF CONSERVED HOMOLOGY 1 DOMAINS COMPLEXED TO LIGANDS

(71) Applicants: Tatyana I. Igumenova, College Station, TX (US); Sachin S. Katti, College Station, TX (US)

(72) Inventors: Tatyana I. Igumenova, College Station, TX (US); Sachin S. Katti, College Station, TX (US)

(*) Notice: Subject to any disclaimer, the term of this patent is extended or adjusted under 35 U.S.C. 154(b) by 192 days.

(21) Appl. No.: 17/900,740

(22) Filed: Aug. 31, 2022

(65) Prior Publication Data

US 2023/0063427 A1 Mar. 2, 2023

Related U.S. Application Data

(60) Provisional application No. 63/239,986, filed on Sep. 2, 2021.

(51) Int. Cl.
| | | |
|---|---|---|
| C30B 29/58 | (2006.01) | |
| C07K 1/30 | (2006.01) | |
| C30B 7/00 | (2006.01) | |

(52) U.S. Cl.
CPC ............. *C07K 1/306* (2013.01); *C30B 7/00* (2013.01); *C30B 29/58* (2013.01)

(58) Field of Classification Search
CPC ............ C30B 7/00; C30B 29/54; C30B 29/58
See application file for complete search history.

(56) References Cited

U.S. PATENT DOCUMENTS

| | | | |
|---|---|---|---|
| 4,235,796 A | 11/1980 | Paulicka | |
| 9,556,217 B2 | 1/2017 | Gellman et al. | |
| 2006/0014934 A1* | 1/2006 | Everse | G01N 33/86 702/19 |
| 2006/0234246 A1* | 10/2006 | Scott | C12Q 1/6886 435/325 |
| 2009/0087436 A1* | 4/2009 | Roch | A61K 31/7052 424/139.1 |

(Continued)

FOREIGN PATENT DOCUMENTS

WO 2006036772 A2 4/2006

OTHER PUBLICATIONS

Kiriazis et al "Stereoselective synthesis of (3-aminodecahydro-1,4-methanonaphthalen-2-yl) methanols targeted to the C1 domain of protein kinase C" Tetrahedron vol. 67, 2011 pp. 8665-8670.*

(Continued)

*Primary Examiner* — Robert M Kunemund
(74) *Attorney, Agent, or Firm* — Yuri A. Gruzdkov

(57) ABSTRACT

A crystallization method for making high-quality molecular crystals containing complexes of diacylglycerol (DAG)-effector proteins and ligands thereof. For example, some of such crystals are of a quality sufficient for crystal-structure determination by X-ray crystallography with a spatial resolution of at least 3.0 Å or, in some cases, of about 1 Å. At least some embodiments of the crystallization method and of the molecular crystals produced thereby can beneficially be used, e.g., to provide high-resolution guides for the design and development of exogenous agonists of DAG-effector proteins of therapeutic interest.

20 Claims, 6 Drawing Sheets

(56) References Cited

U.S. PATENT DOCUMENTS

2017/0348336 A1* 12/2017 Acevedo-Duncan ........................ G01N 33/5743

OTHER PUBLICATIONS

Stewart et al "Interfacial Partitioning of a Loop Hinge Residue Contributes to Diacylglycerol Affinity of Conserved Region 1 Domains*" The Journal of Biological Chemistry vol. 289, No. 40, pp. 27653-27664, Oct. 3, 2014.*

Hirai et al "Importance of Interaction between C1 Domain and Lipids in Protein Kinase Cα Activation: Hydrophobic Side Chain Direction in Isobenzofuranone Ligands ControlsEnzyme Activation Level" ChemMedChem 2007, 2, 1006-1009.*

Nakagawa, Yu, et al. "A Simple Analogue of Tumor-Promoting Aplysiatoxin Is an Antineoplastic Agent Rather Than a Tumor Promoter: Development of a Synthetically Accessible Protein Kinase C Activator with Bryostatin-like Activity.." Journal of the American Chemical Society 131.22 (2009): 7573-7579.

Pettersen, Eric F., et al. "UCSF Chimera—a visualization system for exploratory research and analysis." Journal of computational chemistry 25.13 (2004): 1605-1612.

Rahman, Ghazi M., et al. "Identification of the activator-binding residues in the second cysteine-rich regulatory domain of protein kinase Cθ (PKCθ)." Biochemical Journal 451.1 (2013): 33-44.

Rosse, Carine, et al. "PKC and the control of localized signal dynamics." Nature Reviews Molecular Cell Biology 11.2 (2010): 103-112.

Kazanietz, Marcelo G., editor. "Protein Kinase C in Cancer Signaling and Therapy." Springer Science & Business Media, ISBN 978-1-60761-542-2 (2010): 1-492.

Ryckbosch, Steven M., et al. "Molecular dynamics simulations reveal ligand-controlled positioning of a peripheral protein complex in membranes." Nature Communications 8.1 (2017): 1-10.

Saraiva, Lucília, et al. "Characterization of phorbol esters activity on individual mammalian protein kinase C soforms, using the yeast phenotypic assay." European Journal of Pharmacology 491.2-3 (2004): 101-110.

Sigano, Dina M., et al. "Differential binding modes of diacylglycerol (DAG) and DAG lactones to protein kinase C (PK-C)." Journal of Medicinal Chemistry 46.9 (2003): 1571-1579.

Sloane, Jack L., et al. "Prodrugs of PKC modulators show enhanced HIV latency reversal and an expanded therapeutic window." Proceedings of the National Academy of Sciences 117.20 (2020): 10688-10698.

Spivak, Adam M., et al. "Synthetic Ingenols Maximize Protein Kinase C-Induced HIV-1 Latency Reversal." Antimicrobial Agents and Chemotherapy 62.11 (2018): e01361-18.

Stewart, Mikaela D., et al. "Probing the determinants of diacylglycerol binding affinity in the C1B domain of protein kinase Cα." Journal of Molecular Biology 408.5 (2011): 949-970.

Stewart, Mikaela D., et al. "Interfacial partitioning of a loop hinge residue contributes to diacylglycerol affinity of conserved region 1 domains." Journal of Biological Chemistry 289.40 (2014): 27653-27664.

Stewart, Mikaela D., et al. "Toggling of Diacylglycerol Affinity Correlates with Conformational Plasticity in C1 Domains." Biochemistry 56.21 (2017): 2637-2640.

Wender, Paul A., et al. "Practical Synthesis of Prostratin, DPP, and Their Analogs, Adjuvant Leads Against Latent HIV." Science 320. 5876 (2008): 649-652.

Xu, Junjie, et al. "Mechanistic insights into neurotransmitter release and presynaptic plasticity from the crystal structure of Munc13-1 C1C2BMUN." eLife 6.e22567 (2017): 1-27.

Zhang, Gongyi, et al. "Crystal-Structure of the Cys2 Activator-Binding Domain of Protein-Kinase C-Delta in Complex with Phorbol Ester." Cell 81.6 (1995): 917-924.

Zhang, Gongyi, et al. "Crystallization of the Protein Kinase Cσ C1B Domain." Protein Kinase C Protocols. Methods in Molecular Biology 223 (2003): 299-304.

Zhao, Zhuoshen, et al. "Myotonic dystrophy kinase-related Cdc42-binding kinases (MRCK), the ROCK-like effectors of Cdc42 and Rac1." Small GTPases 6.2 (2015): 81-88.

Ziemba, Brian P., et al. "1H, 13C and 15N Nmr assignments of the C1A and C1B subdomains of PKC-delta." Biomolecular NMR Assignments 5.2 (2011): 125-129.

Ziemba, Brian P., et al. "Single-molecule studies reveal a hidden key step in the activation mechanism of membrane- bound protein kinase C-α. " Biochemistry 53.10 (2014): 1697-1713.

Busto, Jon V., et al. "Surface-active properties of the antitumour ether lipid 1-O-octadecyl-2-O-methyl-rac-glycero-3- phosphocholine (edelfosine)." Biochimica et Biophysica Acta (BBA)-Biomembranes 1768.7 (2007): 1855-1860.

Goñi, Fèlix M., et al. "Structure and functional properties of diacylglycerols in membranes." Progress in Lipid Research 38.1 (1999): 1-48.

Hauser, Helmut. "Short-chain phospholipids as detergents." Biochimica et Biophysica Acta (BBA)—Biomembranes 1508.1-2 (2000): 164-181.

Hutchinson, James M., et al. "Dodecyl-B-melibioside Detergent Micelles as a Medium for Membrane Proteins." Biochemistry 56.41 (2017): 5481-5484.

Hutchinson, James M., et al. "Bicelles Rich in both Sphingolipids and Cholesterol and Their Use in Studies of Membrane Proteins." Journal of the American Chemical Society 142.29 (2020): 12715-12729.

Kallick, Deborah A., et al. "The Use of Dodecylphosphocholine Micelles in Solution NMR." Journal of Magnetic Resonance, Series B 109.1 (1995): 60-65.

Kessi, J., et al. "Short-Chain Phosphatidylcholines as Superior Detergents in Solubilizing Membrane Proteins and Preserving Biological Activity." Biochemistry 33.35 (1994): 10825-10836.

Leikin, S., et al. "Measured effects of diacylglycerol on structural and elastic properties of phospholipid membranes." Biophysical Journal 71.5 (1996): 2623-2632.

Le Maire, Marc, et al. "Interaction of membrane proteins and lipids with solubilizing detergents." Biochimica et Biophysica Acta (BBA) -Biomembranes 1508.1-2 (2000): 86-111.

Nollert, Peter. "Membrane protein crystallization in amphiphile phases: practical and theoretical considerations." Progress in Biophysics and Molecular Biology 88.3 (2005): 339-357.

Ujwal, Rachna, et al. "Crystallizing membrane proteins using lipidic bicelles." Methods 55.4 (2011): 337-341.

Valenzuela-Oses, Johanna K., et al. "Development and characterization of miltefosine-loaded polymeric micelles for cancer treatment." Materials Science and Engineering: C 81 (2017): 327-333.

Abel, Erika L., et al. "Multi-stage chemical carcinogenesis in mouse skin: Fundamentals and applications." Nature Protocols 4.9 (2009): 1350-1362.

Antal, Corina E., et al. "Intramolecular conformational changes optimize protein kinase C signaling." Chemistry & Biology 21.4 (2014): 459-469.

Bertolini, Thomas M., et al. "Protein Kinase C Translocation by Modified Phorbol Esters with Functionalized Lipophilic Regions." The Journal of Organic Chemistry 68.13 (2003): 5028-5036.

Carrasco, Silvia, et al. "Diacylglycerol, when simplicity becomes complex." Trends in Biochemical Sciences 32.1 (2007): 27-36.

Castagna, Monique, et al. "Direct Activation of Calcium-Activated, Phospholipid-Dependent Protein-Kinase by Tumor-Promoting Phorbol Esters." Journal of Biological Chemistry 257.13 (1982): 7847-7851.

Choi, Yongseok, et al. "Conformationally Constrained Analogues of Diacylglycerol (DAG). 28. DAG-dioxolanones Reveal a New Additional Interaction Site in the C1b Domain of PKCσ." Journal of Medicinal Chemistry 50.15 (2007): 3465-3481.

Cooke, Mariana, et al. "Characterization of AJH-836, a diacylglycerol-lactone with selectivity for novel PKC sozymes." Journal of Biological Chemistry 293.22 (2018): 8330-8341.

Delaglio, Frank, et al. "NMRPipe: a multidimensional spectral processing system based on UNIX pipes." Journal of Biomolecular NMR 6.3 (1995): 277-293.

(56) References Cited

OTHER PUBLICATIONS

Dries, Daniel R., et al. "A single residue in the C1 domain sensitizes novel protein kinase C isoforms to cellular diacylglycerol production." Journal of Biological Chemistry 282.2 (2007): 826-830.
Ebinu, Julius O., et al. "RasGRP, a Ras guanyl nucleotide-releasing protein with calcium-and diacylglycerol-binding motifs." Science 280.5366 (1998): 1082-1086.
Emsley, Paul, et al. "Coot: model-building tools for molecular graphics." Acta Crystallographica Section D: Biological Crystallography 60.12 (2004): 2126-2132.
Evans, Philip. "Scaling and assessment of data quality." Acta Crystallographica Section D: Biological Crystallography 62.1 (2006): 72-82.
Evans, Philip R., et al. "How good are my data and what is the resolution?." Acta Crystallographica Section D: Biological Crystallography 69.7 (2013): 1204-1214.
Gutierrez-Uzquiza, Alvaro, et al. "Coordinated activation of the Rac-GAP β2-chimaerin by an atypical proline-rich domain and diacylglycerol." Nature Communications 4.1 (2013): 1-13.
Hanke, C. William, et al. "Efficacy and safety of ingenol mebutate gel in field treatment of actinic keratosis on full face, balding scalp, or approximately 250 cm2 on the chest: A phase 3 randomized controlled trial." Journal of the American Academy of Dermatology 82.3 (2020): 642-650.
Hardman, Clayton, et al. "Synthesis and evaluation of designed PKC modulators for enhanced cancer Immunotherapy." Nature Communications 11.1 Article 1879 (2020): 1-11.
Hatzakis, Emmanuel, et al. "High-resolution NMR spectroscopy: an alternative fast tool for qualitative and quantitative analysis of diacylglycerol (DAG) oil." Journal of the American Oil Chemists' Society 88.11 (2011): 1695-1708.
Hurley, James H., et al. "Taxonomy and function of C1 protein kinase C homology domains." Protein Science 6.2 (1997): 477-480.
Igumenova, Tatyana I. "Dynamics and membrane interactions of protein kinase C." Biochemistry 54.32 (2015): 4953-4968.
Iwahara, Junji, et al. "Ensemble approach for NMR structure refinement against (1)H paramagnetic relaxation enhancement data arising from a flexible paramagnetic group attached to a macromolecule." Journal of the American Chemical Society 126.18 (2004): 5879-5896.
Kabsch, Wolfgang. "XDS." Acta Crystallographica Section D: Biological Crystallography 66.2 (2010): 125-132.
Katti, Sachin, et al. "Partial Metal Ion Saturation of C2 Domains Primes Synaptotagmin 1-Membrane Interactions." Biophysical Journal 118.6 (2020): 1409-1423.
Katti, Sachin, et al. "Structural insights into C1-ligand interactions: Filling the gaps by in silico methods." Advances in Biological Regulation 79, Article 100784 (2021): 1-40.
Kazanietz, M. G., et al. "Differential irreversible insertion of protein kinase C into phospholipid vesicles by phorbol esters and related activators." Journal of Biological Chemistry 267.29 (1992): 20878-20886.
Kazanietz, Marcelo G., et al. "Residues in the Second Cysteine-rich Region of Protein Kinase C d Relevant to Phorbol Ester Binding as Revealed by Site-directed Mutagenesis." Journal of Biological Chemistry 270.37 (1995): 21852-21859.
King, E. J. "XXXIII. The colorimetric determination of phosphorus." Biochemical Journal 26 (1932): 292-297.
Kleis-San Francisco, Susan, et al. "Role of Protein Kinase C Activation in Oocyte Maturation and Steroidogenesis in Ovarian Follicles of Rana pipiens: Studies With Phorbol 12-Myristate 13-Acetate" Gamete Research 21.3 (1988): 323-334.
Laskowksi, Roman A., et al."LigPlot+: multiple ligand-protein interaction diagrams for drug discovery." Journal of Chemical Information and Modeling 51.10 (2011): 2778-2786.
Lebedev, Andrey A., et al. "JLigand: a graphical tool for the CCP4 template-restraint library." Acta Crystallographica Section D: Biological Crystallography 68.4 (2012): 431-440.\.
Lee, Woonghee, et al. "NMRFAM-SPARKY: enhanced software for biomolecular NMR spectroscopy." Bioinformatics 31.8 (2015): 1325-1327.
Li, Jianing, et al. "Interactions of Protein Kinase C-α C1A and C1B Domains with Membranes: A Combined Computational and Experimental Study." Journal of the American Chemical Society 136.33 (2014): 11757-11766.
Liebschner, Dorothee, et al. "Polder maps: improving OMIT maps by excluding bulk solvent." Acta Crystallographica Section D: Structural Biology 73.2 (2017): 148-157.
Liebschner, Dorothee, et al. "Macromolecular structure determination using X-rays, neutrons and electrons: recent developments in Phenix." Acta Crystallographica Section D: Structural Biology 75.10 (2019): 861-877.
Ly, Calvin, et al. "Bryostatin 1 Promotes Synaptogenesis and Reduces Dendritic Spine Density in Cortical Cultures through a PKC-Dependent Mechanism." ACS Chemical Neuroscience 11.11 (2020): 1545-1554.
Ma, Qianqian, et al. "Diacylglycerol kinases: Relationship to other lipid kinases." Advances in Biological Regulation 71 (2019): 104-110.
Marley, Jonathan, et al. "A method for efficient isotopic labeling of recombinant proteins." Journal of Biomolecular NMR 20.1 (2001): 71-75.
Melander, Christian, et al. "Forcing an enemy into the open." Nature Chemistry 4.9 (2012): 692-693.
Moriarty, Nigel W., et al. "Electronic Ligand Builder and Optimization Workbench (eLBOW): a tool for ligand coordinate and restraint generation." Acta Crystallographica Section D: Biological Crystallography 65.10 (2009): 1074-1080.

\* cited by examiner

FIG. 3

| Example | #1 | #2 | #3 | #4 | #5 |
|---|---|---|---|---|---|
| Ligand (concentration) | DAG (2.5 mM) | Bryostatin-1 (3 mM) | Bryostatin-1 (3 mM) | PDBu (2.5 mM) | AJH-836 (3 mM) |
| Membrane mimic (concentration) | DPC (20 mM for blocks 102/104, 10 mM for block 108) | Edelfosine (20 mM) | DHPC:Miltefosine 50:50 (20 mM) | DHPC (20 mM) | DHPC (20 mM) |
| Isopropanol % in reservoir solution | 15% | 30% | 30% | 30% | 15% |

500

600

PREPARATION OF CONSERVED HOMOLOGY 1 DOMAINS COMPLEXED TO LIGANDS

CROSS-REFERENCE TO RELATED APPLICATIONS

This application claims the benefit of U.S. Provisional Patent Application No. 63/239,986 filed on 2 Sep. 2021, and entitled "PREPARATION OF CONSERVED HOMOLOGY 1 DOMAINS COMPLEXED TO LIGANDS."

The patented invention was made with Government support under Grant No. R01 GM108998 awarded by U.S. National Institutes of Health (NIH). The Government has certain rights in the patented invention.

BACKGROUND

Various examples relate generally to biochemical and biophysical methods and, more specifically but not exclusively, to preparation of conserved homology 1 (C1) domains complexed to ligands.

C1 domain (also known as phorbol esters/diacylglycerol binding domain) binds an important second messenger diacylglycerol (DAG), as well as certain phorbol esters. More than sixty different human proteins contain one or more C1 domains, which include, for example, a family of serine/threonine protein kinases, collectively known as protein kinase C (PKC). Both DAG and phorbol esters can activate PKC. Some phorbol esters are potent tumor promoters that can cause a variety of physiological changes when present in cells and/or tissues.

SUMMARY

Disclosed herein are, among other things, various aspects, features, and embodiments of a crystallization method for making high-quality molecular crystals containing complexes of DAG-effector proteins and ligands (e.g., agonists or inhibitors) thereof. For example, some of such crystals are of a quality sufficient for crystal-structure determination by X-ray crystallography with a spatial resolution of at least 3.0 Å or, in some cases, of about 1 Å. At least some embodiments of the crystallization method and of the molecular crystals produced thereby can beneficially be used, e.g., to provide high-resolution guides for the design and development of exogenous agonists of DAG-effector proteins of therapeutic interest.

One example provides a method, comprising the steps of: preparing an aqueous solution including a protein, a ligand, and a membrane mimic, the protein comprising a conserved homology 1 (C1) domain, the ligand being a ligand of the C1 domain, the membrane mimic being selected to facilitate formation of a complex of the C1 domain and the ligand; and placing the aqueous solution in a protein-crystallization arrangement configured to form a crystal including the complex of the protein and the ligand.

In some instances of the above method, the crystal further includes the membrane mimic associated with the complex.

Another example provides a molecular crystal produced using an embodiment of the above method.

Yet another example provides a crystal, comprising: a complex of a protein and a ligand, the protein comprising a conserved homology 1 (C1) domain, the ligand being a ligand of the C1 domain; and a membrane mimic associated with the complex.

Yet another example provides a crystal comprising a complex of a protein and a ligand, the protein comprising a conserved homology 1 (C1) domain, the ligand being a ligand of the C1 domain; and wherein the ligand is selected from the group consisting of: diacylglycerol (DAG); a DAG lactone; a phorbol ester; an ingenol ester; a teleocidin; benzolactam-V8; a benzolactam analog; a mezerein analog; an aplysiatoxin analog; an isophthalate; prostratin; a bryostatin; and a bryostatin analog.

BRIEF DESCRIPTION OF THE DRAWINGS

Other aspects, features, examples, embodiments, and benefits will become more fully apparent, by way of example, from the following detailed description and the accompanying drawings, in which:

FIG. 3 is a table illustrating several specific examples of the crystallization method of FIG. 1.

DETAILED DESCRIPTION

Figure 1:
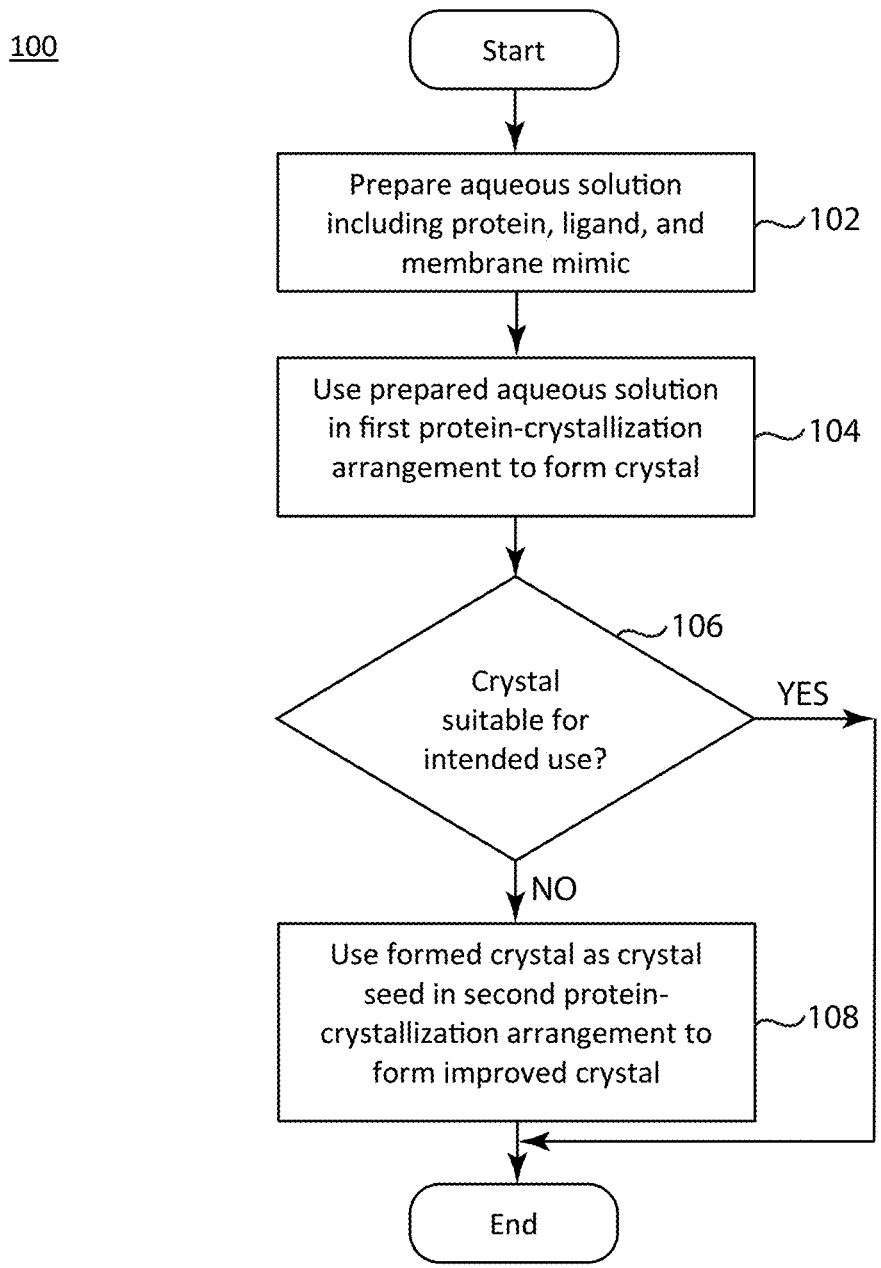
FIG. 1 is a flowchart illustrating a crystallization method according to various examples.

In the following description, numerous details are set forth, such as example compositions of matter, example apparatus, example methods, and the like, in order to provide an understanding of one or more aspects of the present disclosure. It will be readily apparent to a person of ordinary skill in the pertinent art that these specific details are mere examples that are not intended to limit the scope of this application.

Any numerical range recited herein includes all values from the lower value to the upper value. For example, if a range is stated as 1% to 50%, it is intended that the narrower ranges thereof, such as 2% to 40%, 10% to 30%, 1% to 3%, etc., are expressly enumerated by said statement. These specific examples represent only a limited subset of what is intended to be covered, and all possible combinations of numerical values between and including the lowest value and the highest value of the enumerated range are to be considered to be expressly stated in this application. Concentration ranges, pH ranges, and other ranges of specific parameters are intended to be interpreted in a manner similar to the "%" example.

The modifier "about" or "approximately" used in connection with a quantity is inclusive of the stated value and has the meaning dictated by the context (for example, it includes at least the degree of error associated with the measurement of the particular quantity). The modifiers "about." "approximately" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so that, for example "about 1" may also mean from 0.5 to 1.4.

Definitions of specific functional groups and chemical terms pertinent to this disclosure are described in more detail below. For purposes of this disclosure, the chemical elements are identified in accordance with the Periodic Table of the Elements, CAS version, Handbook of Chemistry and Physics, 75th Ed., inside cover, and specific functional groups are generally defined as described therein. Additionally, the present disclosure relies on general principles of organic chemistry, inorganic chemistry, and material science, as accepted in the pertinent arts. For example, specific functional moieties and reactivity in accordance with some of such principles are described in Organic Chemistry, Thomas Sorrell, University Science Books, Sausalito, 1999; Smith and March, March's Advanced Organic Chemistry, 5th Edition, John Wiley & Sons, Inc., New York, 2001; Larock, Comprehensive Organic Transformations, VCH Publishers, Inc., New York, 1989; Carruthers, Some Modern Methods of Organic Synthesis, 3rd Edition, Cambridge University Press, Cambridge, 1987, the entire contents of each of which are incorporated herein by reference.

DAG is a versatile lipid whose 1,2-sn-stereoisomer serves both as a second messenger in signal transduction pathways that control certain cellular processes, and as a metabolic precursor for downstream signaling lipids, such as phosphatidic acid. DAG-effector proteins compete for available lipid using C1 domains as DAG-sensing modules. Yet, understanding how C1 domains recognize and capture DAG and other ligands in the complex environment of a biological membrane is a difficult problem.

The diversity of DAG signaling output is mediated via DAG's interactions with at least seven families of DAG-effector proteins that execute broad sets of regulatory functions. Examples of such regulatory functions include: protein phosphorylation (PKCs and PKDs); DAG phosphorylation (DGKs); RacGTPase activation (chimaerins); Ras guanine nucleotide exchange factor activation (RasGRPs); and assembly of scaffolds that potentiate synaptic vesicle fusion and neurotransmitter release (Munc13-1). Herein, the abbreviations PKD, DGK, RacGTPase, RasGRPs, and Munc13-1 stand for Protein kinase D, Diacylglycerol kinase, Rac guanosine triphosphate hydrolase, Ras guanyl nucleotide releasing proteins, and Mammalian uncoordinated 13-1, respectively. Each of the above-mentioned proteins includes one or more respective C1 domains.

PKCs define a DAG-sensing node in intracellular phosphoinositide signaling pathways that regulate at least cell growth, differentiation, apoptosis, and motility. Shortly after their discovery, PKCs were identified as cellular receptors for tumor-promoting phorbol esters that bind C1 domains in lieu of DAG. These observations, in view of the important roles of PKCs in intracellular signaling, established C1 domains' DAG-sensing function as an attractive target for therapeutic intervention. For example, the targeting of PKC C1 domains for pharmaceutical modulation shows considerable promise in the treatment of Alzheimer's disease, HIV/AIDS, and cancer. However, the structural basis of DAG recognition by C1 domains remained elusive, and representative strategies used for therapeutic agent design typically relied on modeling studies based on limited and/or imprecise structural information.

At least some of the above-indicated problems in the state of the art can beneficially be addressed using at least some embodiments disclosed herein. For example, at least one of such embodiments overcomes a well-documented challenge that hindered crystallization of extremely hydrophobic C1-ligand complexes. Some other example embodiments enable determination of high-resolution structures of C1 bound to the endogenous agonist DAG and to certain selected exogenous agonists of therapeutic interest. Such structural information can beneficially be used to detail, for example, mechanisms of stereo-specific recognition of DAG by the C1 domains, functional properties of the corresponding lipid-binding site, and identities of the residues involved in the recognition and capture of DAG and exogenous agonists. Beneficially, at least some embodiments can: (i) provide a structural rationale for the consensus amino acid sequence of DAG-sensitive C1 domains; (ii) provide insight into the origins of DAG sensitivity; (iii) reveal how the hydrophilic/hydrophobic properties of the ligand-binding site enable C1 domains to accommodate chemically diverse ligands; and (iv) provide high-resolution guides for the design of agents that modulate the activities of DAG-effector proteins.

FIG. 1 is a flowchart illustrating a crystallization method 100 according to various examples. In some examples, method 100 can be implemented using a vapor-diffusion protein-crystallization arrangement, such as a hanging-drop arrangement. Various other protein-crystallization arrangements known to persons of ordinary skill in the pertinent art include but are not limited to a micro-batch arrangement, a micro-dialysis arrangement, and a free-interface-diffusion arrangement. For example, various protein-crystallization arrangements are described in Rupp, B. (2009), Biomolecular Crystallography: Principles, Practice, and Application to Structural Biology (1st ed.), Garland Science, which is incorporated herein by reference in its entirety.

The method 100 comprises preparing an aqueous solution including a protein, a ligand, and a membrane mimic (in block 102). The protein comprises or consists of a C1 domain. The ligand is a ligand of the C1 domain. The membrane mimic is selected to enable binding of the ligand to the C1 domain. Typically, the solution further includes one or more additional components examples of which are detailed below, e.g., in reference to FIG. 3.

In some examples, the block 102 includes the steps of: (i) preparing aqueous mixture of the protein and the membrane mimic; (ii) adding the ligand to the mixture; and (iii) stirring and/or mixing the mixture produced at step (ii) to homogeneity. The protein used in the block 102 can comprise or be, e.g., one of the C1 domains of the Protein kinase Cδ isoform, hereafter referred to as the C1Bδ domain. In some other examples, other proteins having one or more C1 domains may also be used. In various examples, the concentration of the protein in the prepared aqueous solution is in the range between about 0.5 mM and about 3 mM. In some specific examples, the concentration of the protein in the prepared aqueous solution is in the range between 1.9 mM and 2.1 mM.

Figure 2:
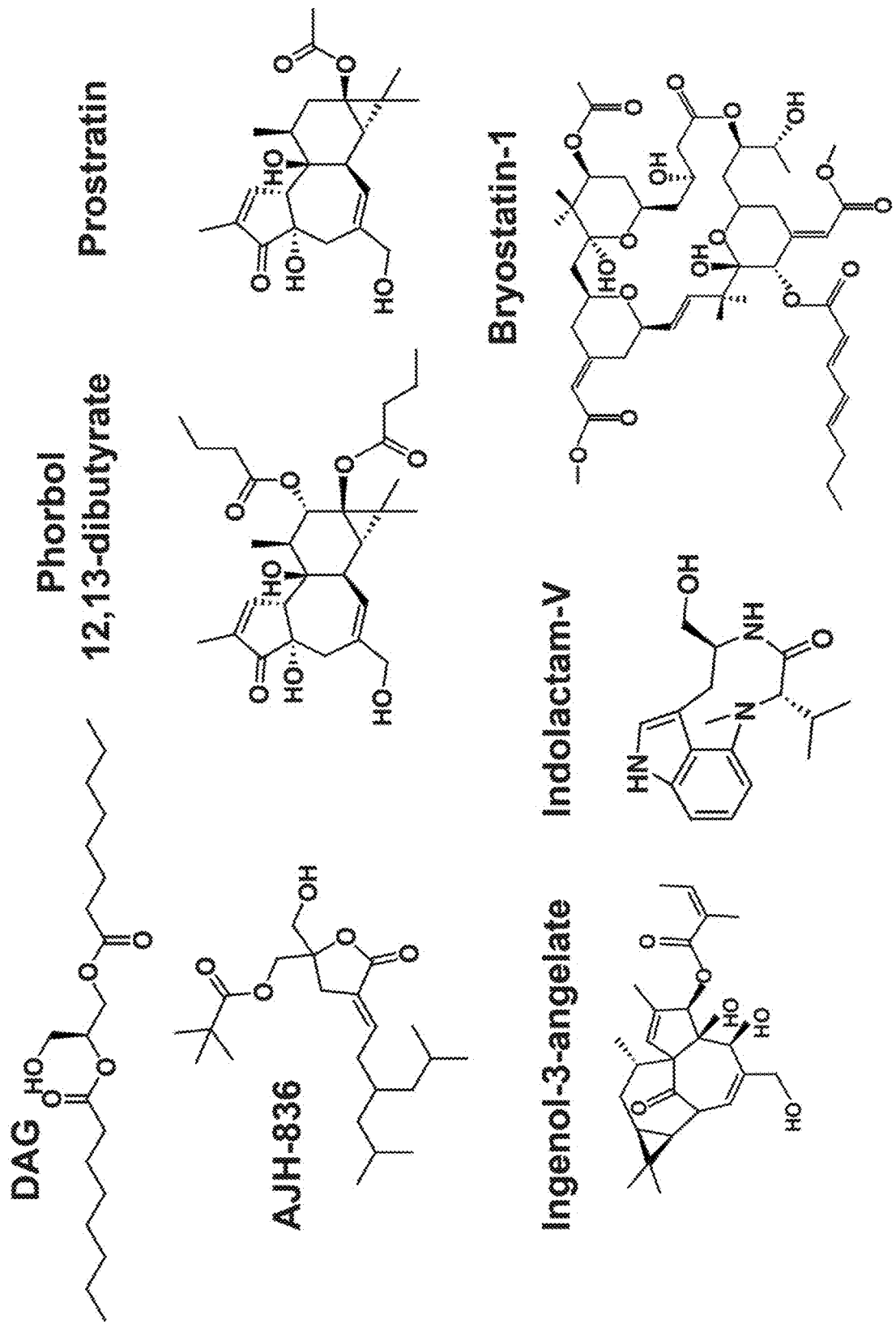
FIG. 2 shows chemical structures of several example ligands that can be used in various embodiments of the crystallization method of FIG. 1.

FIG. 2 shows chemical structures of several example ligands that can be used in the block 102 of the method 100. More specifically, the chemical formulas of DAG, Phorbol-12,13-dibutyrate (PDBu), Prostratin, Bryostatin-1, Ingenol-3-angelate, Indolactam-V, and DAG lactone AJH-836 are shown. In some other examples, other suitable ligands of the C1 domain(s) may similarly be used. Typically, such ligands may fall into the following general categories of chemical compounds: DAG lactones, Phorbol esters, Ingenol esters, Teleocidins, Benzolactam-V8 and analogs, Mezerein analogs, Aplysiatoxin analogs, Isophthalates, and Bryostatins and their analogs, including Bryologs.

As used herein, the term "analog" refers to any compound that is: i) similar in chemical structure to another, and/or ii) designed using retention of one or more protein interacting functional groups of another, and/or iii) designed to retain the predicted pharmacophore elements of another.

Referring back to FIG. 1, in some examples, the membrane mimic used in the block 102 includes one or more phosphocholines, diacylglycerols, detergents, and/or alkyl-lysophospholipid derivatives. Specific examples of these compounds include: dodecylphosphocholine (DPC), 1,2-dioctanoyl-sn-glycerol (DOG), 1,2-diheptanoyl-sn-glycero-3-phosphocholine (DHPC), n-dodecyl-β-D-Melibioside (β-DDMB), Miltefosine, Edelfosine, 1,2-dimyristoyl-sn-glycero-β-phosphocholine (DMPC) in the form of micelles or bicelles. In some specific examples, the membrane mimic comprises at least one of DHPC, Edelfosine, a mixture of DPC and Edelfosine, or a mixture of DPC and DOG. Herein, the term "membrane mimic" refers to an amphipathic detergent or a lipid-based matrix that can form stable aggregates capable of incorporating ligands of interest therein such that the ligand can be accessed by and bound to protein molecules, such as the C1 domains. Examples of such stable aggregates include, but are not limited to, micelles, bicelles, lipid disks, liposomes, and the like, e.g., formed using some of the aforementioned components.

In some examples of the block 102, the prepared aqueous solution has a 1:x:y molar ratio of the protein, ligand, and membrane mimic, where x>0.1 and y>0.5. In some specific examples of the block 102, the aqueous solution has an approximately 1:1.2:10 molar ratio of the protein, ligand, and membrane mimic. In some other specific examples of the block 102, the aqueous solution has an approximately 1:1.5:15 molar ratio of the protein, ligand, and membrane mimic.

In some specific examples of the block 102, the prepared aqueous solution includes one or more of the following buffer components: 50 mM MES pH 6.5, 150 mM KCl, and 1.0 mM TCEP. In various alternative embodiments, other suitable buffers can also be used. Herein, the abbreviation MES stands for 2-(N-morpholino) ethanesulfonic acid; and the acronym TCEP stands for Tris (2-carboxyethyl) phosphine.

The method 100 further comprises using the aqueous solution prepared in the block 102 and a precipitant in a protein-crystallization arrangement and allow for sufficient time to cause formation of a crystal (in block 104). The formed crystal includes a complex of the protein and ligand and further typically includes the membrane mimic associated with the complex. Representative nonlimiting examples of sufficient time for the crystallization process of the block 104 are in the range between about 10 hours (e.g., overnight) and several (e.g., 2 to 4) days.

In one specific example of the block 104, the protein-crystallization arrangement is a hanging-drop vapor-diffusion arrangement, in which a hanging drop made using the aqueous solution prepared in the block 102 is positioned against a liquid reservoir of "reservoir solution" containing a precipitant. In some specific examples, the precipitant comprises ammonium acetate, sodium phosphate, and an alkyl alcohol, e.g., isopropanol. Nonlimiting examples of the chemical compositions of the reservoir solution are further detailed below and indicated in the table shown in FIG. 3. In various specific examples, the hanging drop is made without adding thereto any of the reservoir solution or any prior mixing of the aqueous solution prepared in the block 102 with the reservoir solution. In the corresponding specific instances of such examples, the hanging drop consists of the aqueous solution prepared in the block 102 and, as such, does not contain the alkyl alcohol, ammonium acetate, or sodium phosphate at the time when the corresponding well is closed and sealed. During the above-mentioned "sufficient time" in the block 104, the equilibration processes inside the sealed well cause composition changes in the hanging drop. At some point (in the block 104), the hanging drop reaches a composition that favors crystallization, which causes one or more crystals to form therein.

In some embodiments, a small amount of the alkyl alcohol may be added to the aqueous solution formed in the block 102 or to the hanging drop before the well is closed and sealed. Typically, the amount is small in the sense that the initial concentration of the alkyl alcohol in the hanging drop is smaller or much smaller than the concentration of the alkyl alcohol in the reservoir solution.

In some specific examples of the blocks 102 and 104, the following specific operations are performed. A cDNA segment encoding the C1B6 domain from *Rattus norvegicus* (amino acids 229-281) is subcloned into pET SUMO expression vector (Invitrogen). The $His_6$-SUMO-C1Bδ fusion protein is expressed in *Escherichia coli* BL21(DE3) Rosetta2 cells (Millipore Sigma). The cells are grown in LB broth until $OD_{600}$=0.6, followed by the induction of protein expression with 0.5 mM IPTG at 18° C. for 16 hours. Cell harvesting, lysis, and C1Bδ purification are carried using conventional procedures. The purified protein is stored at 4° C. in the "storage buffer" comprising 50 mM MES at pH 6.5, 150 mM KCl, and 1 mM TCEP, until its use in further operations of the blocks 102 and 104.

Herein, the acronym cDNA stands for complementary Deoxyribonucleic acid; the acronym pET SUMO stands for pET Small Ubiquitin-like modifier; the acronym $His_6$-SUMO-C1Bδ stands for Hexa-Histidine-Small Ubiquitin-like modifier-C1Bδ; the acronym LB stands for Luria-Bertani; the acronym $OD_{600}$ stands for optical density and 600 nm; the acronym IPTG stands for Isopropyl β-D-1-thiogalactopyranoside; the acronym MES stands for 2-(N-morpholino) ethanesulfonic acid; and the acronym TCEP stands for Tris (2-carboxyethyl) phosphine.

In some specific examples of the block 102, to form C1Bδ-ligand complexes in solution, appropriate reagents are combined at a molar ratio of C1Bδ:Ligand:(membrane mimic)=1:1.2:10, where the ligand is PDBu, prostratin, ingenol 3-angelate, or AJH-836. In some instances of the block 102, to achieve full saturation of C1Bδ with AJH-836, additional condition with AJH-836 is used, according to which C1Bδ:AJH-836:DHPC=1:1.5:10. The membrane mimic is in the form of DPC and DHPC micelles prepared using a conventional procedure. 30 mM stock solution of DAG is prepared in DMSO. Herein, the acronym DMSO stands for dimethyl sulfoxide.

In some specific examples of the block 104, C1Bδ complexes with agonists are crystallized at a temperature in the range from 1° C. to 17° C. (e.g., at 4° C.) using a hanging-drop vapor-diffusion method. The crystals of the C1Bδ-ligand complexes typically appear overnight when the ligand is PDBu, prostratin, or ingenol 3-angelate. The crystals of the C1Bδ-ligand complexes typically appear after approximately 1-2 days when the ligand is AJH-836. One or more of the crystals are selected and removed from the hanging-drop vapor-diffusion arrangement (in the block 104) for further use.

The method 100 further comprises a decision block 106, in which it is decided whether or not a crystal formed in the block 104 is suitable for intended use. Example decision criteria applicable for the decision block 106 may include, but are not limited to determining whether or not the crystal is of sufficient size/quality and/or determining whether or not the crystal is of suitable chemical composition. When it is determined that the crystal is suitable for the intended use ("Yes" at the decision block 106), the method 100 is terminated. When it is determined that the crystal is not suitable for the intended use ("No" at the decision block 106), operations of the method 100 are continued in block 108.

The method 100 comprises using the crystal obtained in the block 104 as a crystal seed in a second protein-crystallization arrangement (in the block 108). For example, in some specific instances of the method 100, the first protein-crystallization arrangement used in the block 104 is a first hanging-drop vapor-diffusion arrangement, and the second protein-crystallization arrangement used in the block 108 is a second hanging-drop vapor-diffusion arrangement. In various specific examples, other suitable selections of the respective first and second protein-crystallization arrangements for the blocks 104 and 108 may also be possible.

In a representative example, the block 108 of the method 100 comprises placing the crystal obtained in the block 104 into another aqueous solution including the same protein and the same membrane mimic as those used in the blocks 102, 104. In some instances of the block 108, said another aqueous solution also includes the same ligand as the ligand used in the blocks 102, 104. In some other instances of the block 108, other selections of the components for said another aqueous solution may also be possible.

In a representative example, the block 108 of the method 100 further comprises allowing for a sufficient crystallization time to grow a larger crystal from the crystal seed. Typical examples of such sufficient crystallization time are in the range between approximately 10 hours and 5 days. At the end of such sufficient crystallization time, an improved (e.g., larger and/or higher-quality) crystal is removed from the second protein-crystallization arrangement for further use, and the method 100 is terminated.

FIG. 3 is a table illustrating several specific examples of the method 100. More specifically, five different specific illustrative examples are presented in the table. In these illustrative examples, the aqueous solution of the block 102 has the C1Bδ domain in the concentration of about 2 mM. In some of the examples, mixtures of two different protein stock solutions are used to prepare said aqueous solution. In some instances, the protein stocks are of different ages (i.e., are prepared at different respective times). Example age differences are in the range between 1 to 6 months. The buffer components of the aqueous solution are 50 mM MES pH 6.5, 150 mM KCl, and 1.0 mM TCEP. The reservoir solution includes 0.2 M ammonium acetate and 0.1 M sodium phosphate at pH 6.8. The precipitant is isopropanol. In other specific examples, other suitable selections can also be made.

Example #1 is applicable to both of the blocks 102 and 108, with the corresponding annotations given in the "Membrane mimic" row of the table. Examples ##2-5 illustrate instances of the method 100 in which the decision in the decision block 106 is "Yes," and the block 108 is bypassed. The selected ligands include DAG, Bryostatin-1, PDBu, and AJH-836. The selected membrane mimics include DPC, DHPC, Edelfosine, and a 50:50 mixture of DHPC and Miltefosine. The portion of isopropanol in the reservoir solution is between 15% and 30% by volume.

Figure 4:
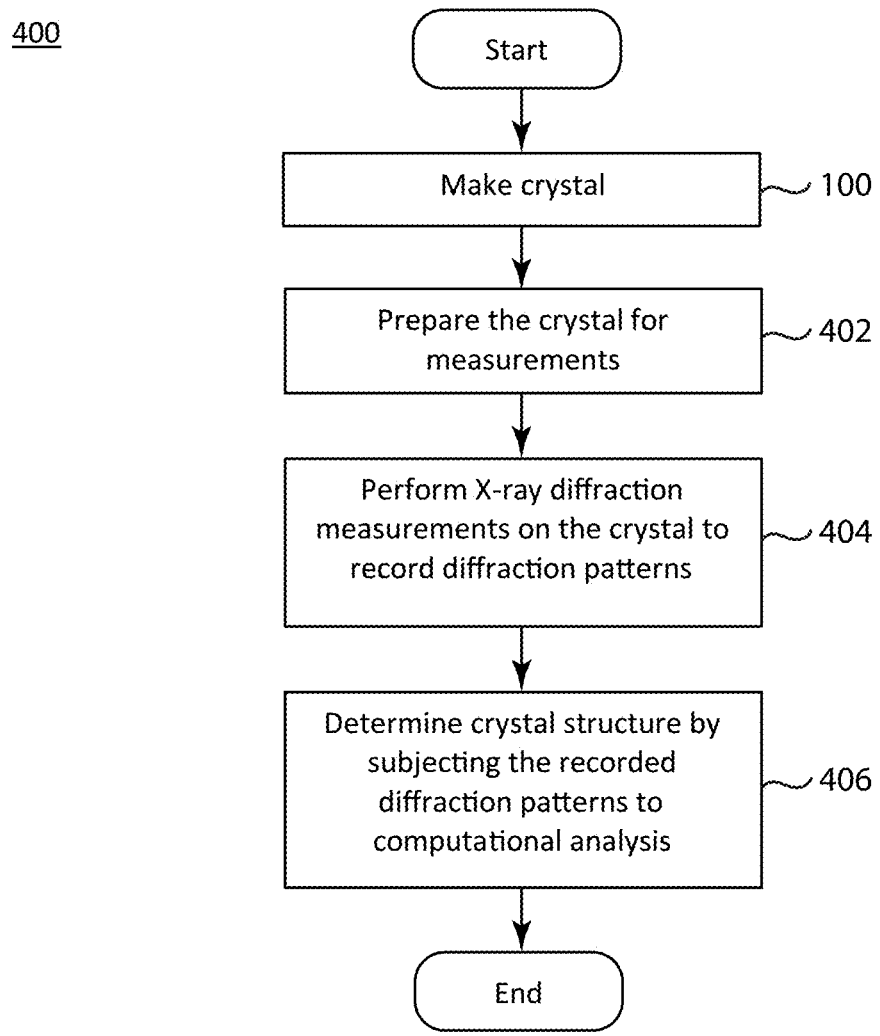
FIG. 4 is a flowchart illustrating a structure-determination method according to various examples.
Figure 5:
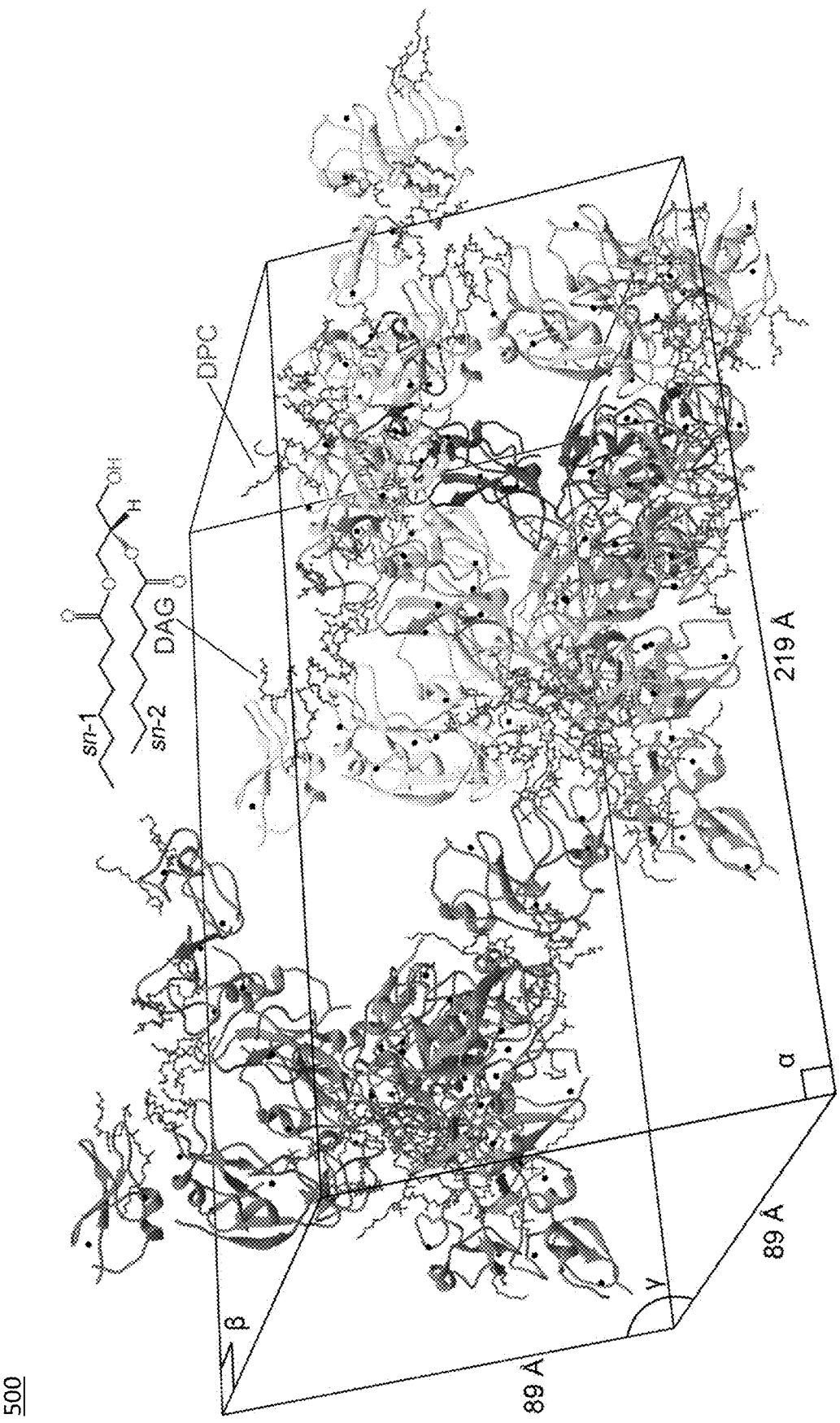
FIG. 5 illustrates a unit cell of an example crystal made using the crystallization method of FIG. 1.
Figure 6:
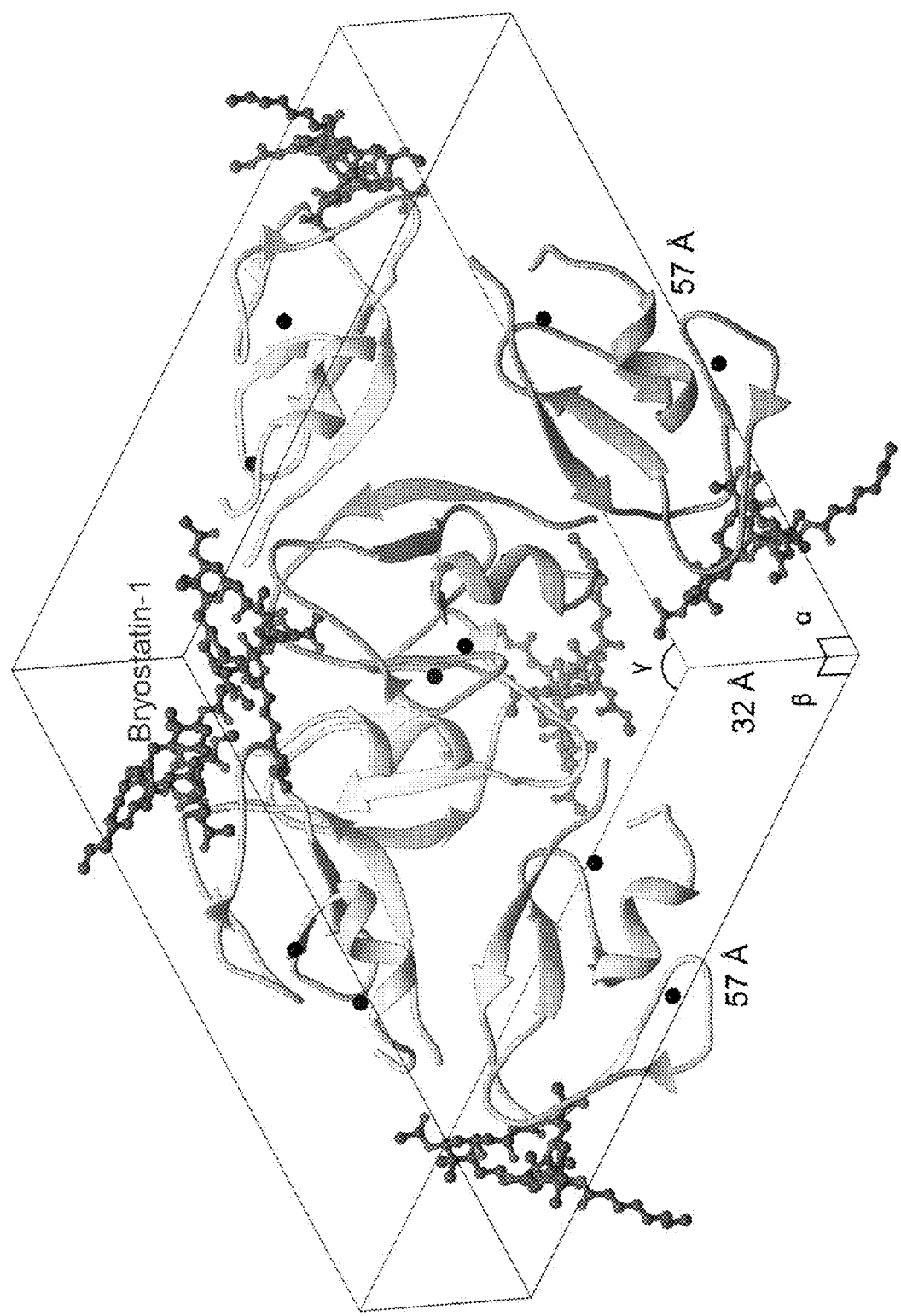
FIG. 6 illustrates a unit cell of another example crystal made using the crystallization method of FIG. 1.

FIG. 4 is a flowchart illustrating a structure-determination method 400 according to various examples. The method 400 includes the method 100 as part thereof and is generally directed at determining structures of the molecular crystals obtained as described above. Representative examples of the crystal structures obtained using the method 400 are shown in FIGS. 5-6.

The method 400 comprises suspending the crystal obtained using the method 100 in a drop of suitable solution containing a cryoprotectant (in block 402). The drop is typically placed in the eye of a small loop configured to act as a sample holder for the intended measurements. The crystal and the loop are typically flash frozen in liquid nitrogen (in the block 402).

The method 400 also comprises performing X-ray diffraction measurements on the loop-mounted crystal (in block 404). In a representative example, the X-ray diffraction measurements in the block 404 include directing a beam of X-rays having a suitable wavelength through the crystal and recording a resulting diffraction pattern using an X-ray detector. The X-ray diffraction measurements in the block 404 further include rotating the crystal by a small angle and repeating the steps of directing the X-ray beam through the crystal and recording the resulting diffraction pattern using the X-ray detector. Such repeated measurements are continued (in the block 404) until different orientations of the crystal sufficiently sample a first desired angular range (e.g., 360 degrees) of rotations about a first selected rotation axis and typically also sufficiently sample a second desired angular range (e.g., 180 degrees) of rotations about a different second rotation axis oriented at a non-zero (e.g., 90-degree) angle with respect to the first rotation axis. In some examples of the block 404, the X-ray beam for the measurements is generated using a synchrotron. In some other examples of the block 404, the X-ray beam is generated using an alternative suitable X-ray source, e.g., a Cu k-alpha X-ray generator.

The method 400 also comprises subjecting the recorded diffraction patterns to computational analysis (in block 406). In a representative example, such computational analysis includes indexing, integrating, merging, and scaling each spot in each diffraction pattern by a computer to produce a corresponding single file from the plurality of diffraction patterns recorded in the block 404. Such computational analysis typically further includes generating an electron-density map, phasing, solving the crystal structures, e.g., by molecular replacement, and performing several iterative cycles of refinement, sometimes aided by manual adjustments. Various software packages for performing different portions of such computational analysis are readily available and known to persons of ordinary skill in the pertinent art. Upon completion of the computational analysis, the method 400 is terminated.

FIG. 5 illustrates a unit cell 500 of an example crystal made using the method 100. The structure of the unit cell 500 is determined using the method 400. In this particular example, the protein, ligand, and membrane mimic are the C1Bδ domain, DAG, and DPC, respectively. The space group of the crystal is H3. In FIG. 5, the protein molecules are represented by ribbon diagrams, also known as Richardson diagrams. DAG molecules are represented by ball-and-stick models. DPC molecules are represented by stick models.

The unit cell 500 has the dimensions of 89.07 Å, 89.07 Å, and 218.68 Å. The unit cell angles are $\alpha=90.0°$, $\beta=90.0°$, and $\gamma=120.0°$. The unit cell 500 includes 72 C1Bδ domains (protein molecules), 72 DAG molecules complexed to the C1Bδ domains, and 18 DAG and 54 DPC molecules peripherally associated with the complexes. Structural $Zn^{2+}$ ions of the C1Bδ domains are shown in FIG. 5 as black dots.

FIG. 6 illustrates a unit cell 600 of another example crystal made using the method 100. The structure of the unit cell 600 is determined using the method 400. In this particular example, the protein, ligand, and membrane mimic are the C1Bδ domain, Bryostatin-1, and DPC:Edelfosine (1:1), respectively. The space group of the crystal is P 61. In FIG. 6, the protein molecules are represented by ribbon diagrams; and Bryostatin-1 molecules are represented by ball-and-stick models.

The unit cell 600 has the dimensions of 57.18 Å, 57.18 Å, and 32.47 Å. The unit cell angles are $\alpha=90.0°$, $\beta=90.0°$, and $\gamma=120.0°$. The unit cell 600 includes six C1Bδ domains and six Bryostatin-1 molecules complexed to the C1Bδ domains. In the rendering of the unit cell 600 shown in FIG. 6, the membrane-mimic molecules are not shown due to the electron density thereof being not sufficiently well-resolved in the electron-density maps. The latter property of the electron-density maps can be due to one or more possible factors, one of which being a relatively small number or absence of the membrane-mimic molecules in the unit cell 600, e.g., due to the unit cell 600 being substantially free of the membrane-mimic molecules.

Herein, the term "substantially free of" a component means that a referred-to composition contains the component in an amount of less than 1% by weight of the composition. This includes less than 0.9% by weight, less than 0.8% by weight, less than 0.7% by weight, and so on, less than 0.1% by weight, less than 0.05% by weight, and less than 0.01% by weight. Compositions "substantially free of" a component also include compositions that are completely free of that component. As a non-limiting example, a composition is understood to be "substantially free" or "free" of a substance, where that substance either is not deliberately added in the process of manufacturing the composition or is present in trace or undetectable amount via contamination or as an impurity resulting from the manufacturing process.

In various example crystals made using the method 100, the following unit cell characteristics are observed (typically but not exclusively). Unit cell volumes are between approximately $5\times10^4$ Å$^3$ and approximately $2\times10^6$ Å$^3$. The number of protein units (molecules) per unit cell is between 4 and about 100. The number of ligand molecules per unit cell is between 4 and about 100. In some examples of the crystals made using the method 100, the unit cell only has ligand molecules complexed to the protein molecules by being bound to the corresponding binding site on the protein. In some other examples of the crystals made using the method 100, the unit cell additionally has one or more ligand molecules that are "loosely" associated with the complexes, i.e., by not being bound to an identifiable binding site on the protein. In the latter examples the ratio of the number of ligand molecules to the number of protein molecules in the unit cell is greater than one. The number of membrane-mimic molecules per unit cell is, in some cases, greater than 50. In some other cases, the number of membrane-mimic molecules per unit cell is between 1 and 50. In yet some other cases, the unit cell is substantially free of membrane-mimic molecules. Example space groups include but are not limited to H3, P 61, C 1 2 1, P 41, and P 21 21 21.

According to an example embodiment disclosed above, e.g., in the summary section and/or in reference to any one or any combination of some or all of FIGS. 1-6, provided is a crystal, comprising: a complex of a protein and a ligand, the protein comprising a conserved homology 1 (C1) domain, the ligand being a ligand of the C1 domain; and a membrane mimic associated with the complex.

In some embodiments of the above crystal, the ligand is selected from the group consisting of: diacylglycerol (DAG); a DAG lactone; a phorbol ester; an ingenol ester; a teleocidin; benzolactam-V8; a benzolactam analog; a mezerein analog; an aplysiatoxin analog; an isophthalate; prostratin; a bryostatin; and a bryostatin analog (e.g., a bryolog).

In some embodiments of any of the above crystals, the ligand is an agonist or inhibitor of the protein, the protein being a DAG-effector protein.

In some embodiments of any of the above crystals, the membrane mimic is selected from the group consisting of: a phosphocholine; a diacylglycerol; a detergent; and an alkyl-lysophospholipid derivative.

In some embodiments of any of the above crystals, the crystal is of a quality sufficient for crystal-structure determination by X-ray crystallography with a spatial resolution of 3.0 Å or finer than 3.0 Å.

In some embodiments of any of the above crystals, the crystal has a unit cell characterized by one or more of the following properties: a volume between $5\times10^4$ Å$^3$ and $2\times10^6$ Å$^3$; a number of protein molecules between 4 and 100; a number of ligand molecules between 4 and 100; a ratio of the number of ligand molecules to the number of protein molecules greater than or equal to one; and a number of membrane-mimic molecules per unit cell between 1 and 60.

In some embodiments of any of the above crystals, a unit cell of the crystal includes a cluster of molecules of the membrane mimic associated with a molecule of the ligand.

According to another example embodiment disclosed above, e.g., in the summary section and/or in reference to any one or any combination of some or all of FIGS. 1-6, provided is a crystal, comprising a complex of a protein and a ligand, the protein comprising a conserved homology 1 (C1) domain, the ligand being a ligand of the C1 domain; and wherein the ligand is selected from the group consisting of: diacylglycerol (DAG); a DAG lactone; a phorbol ester; an ingenol ester; a teleocidin; benzolactam-V8; a benzolactam analog; a mezerein analog; an aplysiatoxin analog; an isophthalate; prostratin; a bryostatin; and a bryostatin analog.

In some embodiments of the above crystal, the crystal is of a quality sufficient for crystal-structure determination by X-ray crystallography with a spatial resolution of 3.0 Å or finer than 3.0 Å.

In some embodiments of any of the above crystals, the crystal has a unit cell characterized by one or more of the following properties: a volume between $5\times10^4$ Å$^3$ and $2\times10^6$ Å$^3$; a number of protein molecules between 4 and 100; a number of ligand molecules between 4 and 100; and a ratio of the number of ligand molecules to the number of protein molecules greater than or equal to one.

According to yet another example embodiment disclosed above, e.g., in the summary section and/or in reference to any one or any combination of some or all of FIGS. 1-6, provided is a method, comprising the steps of: preparing an aqueous solution including a protein, a ligand, and a membrane mimic, the protein comprising a conserved homology 1 (C1) domain, the ligand being a ligand of the C1 domain, the membrane mimic being selected to facilitate formation of a complex of the C1 domain and the ligand; and placing the aqueous solution in a protein-crystallization arrangement configured to form a crystal including the complex of the protein and the ligand.

In some embodiments of the above method, the crystal further includes the membrane mimic associated with the complex.

In some embodiments of any of the above methods, the protein-crystallization arrangement is a vapor-diffusion arrangement; and wherein a reservoir solution in the vapor-diffusion arrangement includes an alkyl alcohol.

In some embodiments of any of the above methods, the alkyl alcohol is isopropanol.

In some embodiments of any of the above methods, the aqueous solution has an approximately 1:1.2:10 molar ratio of the protein, ligand, and membrane mimic.

In some embodiments of any of the above methods, the aqueous solution has a 1:x:y molar ratio of the protein, ligand, and membrane mimic, where x>0.1 and y>0.5.

In some embodiments of any of the above methods, the ligand is selected from the group consisting of: diacylglycerol (DAG); a DAG lactone; a phorbol ester; an ingenol ester; a teleocidin; benzolactam-V8; a benzolactam analog; a mezerein analog; an aplysiatoxin analog; an isophthalate; prostratin; a bryostatin; and a bryostatin analog.

In some embodiments of any of the above methods, the ligand is an agonist or inhibitor of the protein, the protein being a DAG-effector protein.

In some embodiments of any of the above methods and crystals, the protein consists of the C1 domain.

In some embodiments of any of the above methods, the membrane mimic is selected from the group consisting of: a phosphocholine; a diacylglycerol; a detergent; and an alkyl-lysophospholipid derivative.

In some embodiments of any of the above methods and crystals, the membrane mimic is selected from the group consisting of: dodecylphosphocholine (DPC); 1,2-dioctanoyl-sn-glycerol (DOG); 1,2-diheptanoyl-sn-glycero-3-phosphocholine (DHPC); n-dodecyl-β-D-Melibioside (β-DDMB); miltefosine; edelfosine; and 1,2-dimyristoyl-sn-glycero-3-phosphocholine (DMPC).

In some embodiments of any of the above methods, the method further comprises using the crystal as a crystal seed in another protein-crystallization arrangement, which includes placing the crystal into another aqueous solution including the protein, the membrane mimic, and the ligand.

In some embodiments of any of the above methods, the method further comprises allowing for a sufficient crystallization time to grow an improved crystal from the crystal seed.

In some embodiments of any of the above methods, the method further comprises performing X-ray diffraction measurements on the crystal.

According to yet another example embodiment disclosed above, e.g., in the summary section and/or in reference to any one or any combination of some or all of FIGS. 1-6, provided is a molecular crystal produced using any of the above methods.

In some embodiments of any of the above methods and crystals, the protein is a portion of a protein selected from the group including or consisting of: Protein kinase C, Protein kinase D, Diacylglycerol kinase, Rac guanosine triphosphate hydrolase, Ras guanyl nucleotide releasing proteins, and Mammalian uncoordinated 13-1.

It is to be understood that the above description is intended to be illustrative and not restrictive. Many implementations and applications other than the examples provided would be apparent to a person of ordinary skill in the pertinent art upon reading the above description. The scope should be determined, not with reference to the above description, but should instead be determined with reference to the appended claims, along with the full scope of equivalents to which such claims are entitled. It is anticipated and intended that future developments will occur in the technologies discussed herein, and that the disclosed systems, methods, and compositions of matter will be incorporated into such future examples. In sum, it should be understood that the application is capable of modification and variation.

All terms used in the claims are intended to be given their broadest reasonable constructions and their ordinary meanings as understood by those knowledgeable in the technologies described herein unless an explicit indication to the contrary is made herein. In particular, use of the singular articles such as "a," "the," "said," etc. should be read to recite one or more of the indicated elements unless a claim recites an explicit limitation to the contrary.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various examples for the purpose of streamlining the disclosure. This method of disclosure is not to be interpreted as reflecting an intention that the claimed subject matter incorporate more features than are expressly recited in each claim. Rather, as the following claims reflect, inventive subject matter lies in fewer than all features of a single disclosed example. Thus, the following claims are hereby incorporated into the Detailed Description, with each claim standing on its own as a separately claimed subject matter.

While this disclosure includes references to illustrative examples, this specification is not intended to be construed in a limiting sense. Various modifications of the described aspects, features, and examples are possible.

It will be further understood that various changes in the details, materials, and arrangements which have been described and illustrated in order to explain the nature of this disclosure may be made by those skilled in the art without departing from the scope of the disclosure, e.g., as expressed in the following claims.

Although the elements in the following method claims are recited in a particular sequence with corresponding labeling, unless the claim recitations otherwise imply a particular sequence for implementing some or all of those elements, those elements are not necessarily intended to be limited to being implemented in that particular sequence.

Unless explicitly stated otherwise, each numerical value and range should be interpreted as being approximate as if the word "about" or "approximately" preceded the value or range.

What is claimed is:

1. A method, comprising:
   preparing an aqueous solution including a protein, a ligand, and a membrane mimic, the protein comprising a conserved homology 1 (C1) domain, the ligand being a ligand of the C1 domain, the membrane mimic being selected to facilitate formation of a complex of the C1 domain and the ligand; and
   placing the aqueous solution in a protein-crystallization arrangement configured to form a crystal including the complex of the protein and the ligand.

2. The method of claim 1, wherein the crystal further includes the membrane mimic associated with the complex.

3. The method of claim 1,
   wherein the protein-crystallization arrangement is a vapor-diffusion arrangement; and
   wherein a reservoir solution in the vapor-diffusion arrangement includes an alkyl alcohol.

4. The method of claim 3, wherein the alkyl alcohol is isopropanol.

5. The method of claim 1, wherein the aqueous solution has an approximately 1:1.2:10 molar ratio of the protein, ligand, and membrane mimic.

6. The method of claim 1, wherein the aqueous solution has a 1:x:y molar ratio of the protein, ligand, and membrane mimic, where x>0.1 and y>0.5.

7. The method of claim 1, wherein the ligand is selected from the group consisting of:
   diacylglycerol (DAG);
   a DAG lactone;
   a phorbol ester;
   an ingenol ester;
   a teleocidin;
   benzolactam-V8;
   a benzolactam analog;
   a mezerein analog;
   an aplysiatoxin analog;
   an isophthalate;
   prostratin;
   a bryostatin; and
   a bryostatin analog.

8. The method of claim 1, wherein the ligand is an agonist or inhibitor of the protein, the protein being a DAG-effector protein.

9. The method of claim 1, wherein the membrane mimic is selected from the group consisting of:
   a phosphocholine;
   a diacylglycerol;
   a detergent; and
   an alkyl-lysophospholipid derivative.

10. The method of claim 1, further comprising using the crystal as a crystal seed in another protein-crystallization arrangement, which includes placing the crystal into another aqueous solution including the protein, the membrane mimic, and the ligand.

11. The method of claim 1, further comprising performing X-ray diffraction measurements on the crystal.

12. A crystal, comprising:
   a complex of a protein and a ligand, the protein comprising a conserved homology 1 (C1) domain, the ligand being a ligand of the C1 domain; and
   a membrane mimic associated with the complex.

13. The crystal of claim 12, wherein the ligand is selected from the group consisting of:
   diacylglycerol (DAG);
   a DAG lactone;
   a phorbol ester;
   an ingenol ester;
   a teleocidin;
   benzolactam-V8;
   a benzolactam analog;
   a mezerein analog;
   an aplysiatoxin analog;
   an isophthalate;
   prostratin;
   a bryostatin; and
   a bryostatin analog.

14. The crystal of claim 12, wherein the ligand is an agonist or inhibitor of the protein, the protein being a DAG-effector protein.

15. The crystal of claim 12, wherein the membrane mimic is selected from the group consisting of:
   a phosphocholine;
   a diacylglycerol;
   a detergent; and
   an alkyl-lysophospholipid derivative.

16. The crystal of claim 12, wherein the crystal is of a quality sufficient for crystal-structure determination by X-ray crystallography with a spatial resolution of 3.0 Å or finer than 3.0 Å.

17. The crystal of claim 12, wherein the crystal has a unit cell characterized by one or more of the following properties:
   a volume between $5 \times 10^4$ Å$^3$ and $2 \times 10^6$ Å$^3$;
   a number of protein molecules between 4 and 100;
   a number of ligand molecules between 4 and 100;
   a ratio of the number of ligand molecules to the number of protein molecules greater than or equal to one; and
   a number of membrane-mimic molecules per unit cell between 1 and 60.

18. A crystal, comprising a complex of a protein and a ligand, the protein comprising a conserved homology 1 (C1) domain, the ligand being a ligand of the C1 domain; and
   wherein the ligand is selected from the group consisting of:
      diacylglycerol (DAG);
      a DAG lactone;
      an ingenol ester;
      a teleocidin;
      benzolactam-V8;
      a benzolactam analog;
      a mezerein analog;
      an aplysiatoxin analog;
      an isophthalate;
      prostratin;
      a bryostatin; and
      a bryostatin analog.

19. The crystal of claim 18, wherein the crystal is of a quality sufficient for crystal-structure determination by X-ray crystallography with a spatial resolution of 3.0 Å or finer than 3.0 Å.

20. The crystal of claim 18, wherein the crystal has a unit cell characterized by one or more of the following properties:
   a volume between $5 \times 10^4$ Å$^3$ and $2 \times 10^6$ Å$^3$;
   a number of protein molecules between 4 and 100;
   a number of ligand molecules between 4 and 100; and
   a ratio of the number of ligand molecules to the number of protein molecules greater than or equal to one.

* * * * *